United States Patent
Baldwin, Jr. et al.

(10) Patent No.: US 7,208,202 B2
(45) Date of Patent: Apr. 24, 2007

(54) METHODS OF FINISHING MEDICAL BARRIER FABRICS

(75) Inventors: A. Frank Baldwin, Jr., Greensboro, NC (US); David F. Miller, Greensboro, NC (US); Rene Kapik, Greensboro, NC (US)

(73) Assignee: Precision Fabrics Group, Inc., Greensboro, NC (US)

( * ) Notice: Subject to any disclaimer, the term of this patent is extended or adjusted under 35 U.S.C. 154(b) by 0 days.

(21) Appl. No.: 11/282,905

(22) Filed: Nov. 18, 2005

(65) Prior Publication Data

US 2006/0105110 A1 May 18, 2006

Related U.S. Application Data

(60) Provisional application No. 60/629,090, filed on Nov. 18, 2004.

(51) Int. Cl.
*B05D 5/12* (2006.01)
*B05D 1/02* (2006.01)
*B05D 1/18* (2006.01)
*B05D 3/00* (2006.01)
*B05D 3/02* (2006.01)

(52) U.S. Cl. ............... 427/394; 427/209; 427/288; 427/350; 427/421.1; 427/430.1

(58) Field of Classification Search ............... 427/412
See application file for complete search history.

(56) References Cited

U.S. PATENT DOCUMENTS

| | | | |
|---|---|---|---|
| 3,081,519 A | 3/1963 | Blades et al. | |
| 3,338,992 A | 8/1967 | Kinney | |
| 3,411,945 A | 11/1968 | Chao | |
| 3,692,618 A | 9/1972 | Dorschner et al. | |
| 3,802,817 A | 4/1974 | Matsuki et al. | |
| 3,849,241 A | 11/1974 | Buntin et al. | |
| 3,992,144 A | 11/1976 | Jackson | |
| 4,187,390 A | 2/1980 | Gore | |
| 4,307,143 A | 12/1981 | Meitner | |
| 4,340,563 A | 7/1982 | Appel et al. | |
| 4,411,928 A | 10/1983 | Baldwin | |
| 4,663,220 A | 5/1987 | Wisneski et al. | |
| 4,666,764 A | 5/1987 | Kobayashi et al. | |
| 4,822,667 A * | 4/1989 | Goad et al. ............... 442/123 |
| 4,919,998 A * | 4/1990 | Goad et al. ............... 442/123 |
| 5,145,727 A | 9/1992 | Potts et al. | |
| 5,149,576 A | 9/1992 | Potts et al. | |
| 5,178,931 A | 1/1993 | Perkins et al. | |
| 5,178,932 A | 1/1993 | Perkins et al. | |
| 5,397,629 A | 3/1995 | Jahn | |
| 5,441,056 A | 8/1995 | Weber et al. | |
| 5,458,590 A | 10/1995 | Schleinz et al. | |
| 5,482,765 A | 1/1996 | Bradley et al. | |
| 5,503,907 A | 4/1996 | Gessner et al. | |
| 5,534,340 A | 7/1996 | Gupta et al. | |
| 5,560,974 A | 10/1996 | Langley | |
| 5,643,653 A | 7/1997 | Griesbach, III et al. | |
| 5,711,994 A | 1/1998 | Powers | |
| 5,843,057 A | 12/1998 | McCormack | |
| 5,856,245 A * | 1/1999 | Caldwell et al. ............... 442/76 |
| 5,869,172 A * | 2/1999 | Caldwell ............... 428/306.6 |
| 5,874,164 A * | 2/1999 | Caldwell ............... 428/306.6 |
| 5,885,909 A | 3/1999 | Rudisill et al. | |
| 5,899,785 A | 5/1999 | Groten et al. | |
| 5,912,116 A * | 6/1999 | Caldwell ............... 435/5 |
| 5,970,583 A | 10/1999 | Groten et al. | |
| 6,001,749 A | 12/1999 | Child et al. | |
| 6,040,251 A * | 3/2000 | Caldwell ............... 442/123 |
| 6,083,602 A * | 7/2000 | Caldwell et al. ............... 428/77 |
| 6,297,304 B1 | 10/2001 | Raiford et al. | |
| 6,787,184 B2 | 9/2004 | Snowden et al. | |
| 6,833,335 B2 | 12/2004 | DeMott et al. | |
| 6,903,034 B1 | 6/2005 | Putnam et al. | |
| 2002/0019183 A1 | 2/2002 | Demott et al. | |
| 2003/0181113 A1 | 9/2003 | Demott et al. | |
| 2004/0006827 A1 | 1/2004 | Rising | |
| 2004/0102123 A1 | 5/2004 | Bowen, Jr. et al. | |

(Continued)

FOREIGN PATENT DOCUMENTS

WO    WO 96/09165 A1 * 3/1996

(Continued)

OTHER PUBLICATIONS

International Search Report and Written Opinion of the International Searching Authority corresponding to PCT/US2005/041986, mailed Apr. 3, 2006.

(Continued)

*Primary Examiner*—William Phillip Fletcher, III
(74) *Attorney, Agent, or Firm*—Myers Bigel Sibley & Sajovec

(57) ABSTRACT

A method of finishing a barrier fabric includes applying a non-aqueous solution of low surface tension solvent and fluorochemical repellent to a barrier fabric, subjecting the barrier fabric to conditions sufficient to remove the solvent from the barrier fabric, and applying an aqueous-based antistat to a surface of the barrier fabric. The low surface tension solvent substantially covers all fibers in the barrier fabric with the fluorochemical repellent. The antistat is prevented by the fluorochemical from migrating from the surface to which it is applied.

27 Claims, No Drawings

U.S. PATENT DOCUMENTS

| | | | |
|---|---|---|---|
| 2004/0235380 A1* | 11/2004 | Kapik | ............... 442/79 |
| 2005/0112969 A1 | 5/2005 | Snowden et al. | |
| 2005/0112970 A1 | 5/2005 | Snowden et al. | |
| 2005/0181691 A1 | 8/2005 | Klutz | |

FOREIGN PATENT DOCUMENTS

| WO | WO 01/50896 A2 | 7/2001 |
|---|---|---|
| WO | WO 2004/024436 A1 | 3/2004 |
| WO | WO 2004/050354 A1 | 6/2004 |

OTHER PUBLICATIONS

Dantz, Dr. Dirk A., "Antistatic filter media for dust removal," *Nonwovens-Industrial Textiles*, Feb. 2000, pp. 20-24. Supplied by The British Library.

* cited by examiner

METHODS OF FINISHING MEDICAL BARRIER FABRICS

RELATED APPLICATION

This application claims the benefit of and priority to U.S. Provisional Patent Application No. 60/629,090 filed Nov. 18, 2004, the disclosure of which is incorporated herein by reference as if set forth in its entirety.

FIELD OF THE INVENTION

The present invention relates generally to fabrics and, more particularly, to surgical barrier fabrics.

BACKGROUND OF THE INVENTION

The use of synthetic fibers for the production of surgical barrier fabrics is well known. Conventionally, barrier fabrics made from these fibers are treated for repellency to water, blood, body fluids, prep solutions, isopropyl alcohol solutions, and other liquids encountered in medical or surgical practice. In addition to being resistant to wetting and penetration by liquids, barrier fabrics may also be treated for antistatic performance.

A guide for the performance of barrier fabrics is contained in the Association for the Advancement of Medical Instrumentation, Technical Information Report Number 11: *Selection of Gowns and Drapes in Health Care Facilities*, 1994a, which is incorporated herein by reference in its entirety. This guide discusses the importance of liquid repellency and static control for barrier fabrics.

Historically, barrier fabrics used in surgical practice have been cotton or cellulose based. Hospital "linens" conventionally have been based on cotton sheeting or canvas, having an aqueous dispersion with a blend of fluorochemical repellents, wax based repellents and salt type antistats.

Upon the introduction of nonwoven surgical barrier fabrics in the late 1970's, a blend of woodpulp and polyester fibers were spunlaced into fabrics that were finished in a similar way to hospital linens. In these nonwoven barrier fabrics, the woodpulp component conventionally provides the barrier properties and the polyester provides strength.

Around 1980, Kimberly Clark introduced a new type of nonwoven fabric that is commonly known as SMS (spunbond-meltblown-spunbond). SMS fabric is a thermal bonded composite of three nonwoven layers; a top layer of spunbond, a middle layer of meltblown fiber, and a bottom layer of spunbond. SMS fabrics conventionally are made from polypropylene; however, they can be produced from most polymers that are melt spinnable.

The finishing of barrier fabrics with liquid repellent chemistry is well known. Fabrics made from cotton and treated with Quarpel® brand finishes have been extensively used for rainwear, and medical barrier fabrics. Quarpel® brand finishes are water based dispersions of fluorochemical repellent with a stearylol melamine-wax repellent extender. The use of fluorochemical repellents have been used extensively to finish nonwovens and other textiles for a variety of end uses.

Fluorochemical treatment of barrier fabrics, such as SMS fabrics, is described in U.S. Pat. No. 5,441,056 to Weber et al., and U.S. Pat. No. 5,178,932 to Perkins et al., each of which is incorporated herein by reference in its entirety. Conventionally, fluorochemical finishing combines a fluorochemical repellent, a wetting agent, and an antistat in a treating bath.

Fluorochemical treatment is advantageous over silicone or wax type repellents in that the surface energy of the fiber is reduced to a point where isopropanol solutions and oils, commonly encountered in medical use, are repelled. Antistats conventionally are added to improve comfort and reduce the likelihood of an electrostatic spark in an atmosphere of enriched oxygen, or flammable vapor.

Fluorochemical treatments have been dispersed into molten polymer used to spin fiber. For example, see U.S. Pat. No. 5,145,727 to Potts et al., U.S. Pat. No. 5,149,576 to Potts et al., U.S. Pat. No. 5,178,931 to Perkins et al., U.S. Pat. No. 5,178,932 to Perkins et al., and U.S. Pat. No. 6,297,304 to Raiford et al., each of which is incorporated herein by reference in its entirety. The incorporation of fluorochemicals into the melt can be problematic due to decomposition at high spinning temperatures, loss of material to vaporization, and inefficiency of material not at the surface of the fiber. Additionally, the use of a melt antistat may further complicate this process.

Conventional water-based finishing systems contain a fluorochemical dispersion and a wetting agent, and may also contain an antistat. Water-based systems may be efficient in the amount of chemistry required to achieve repellent properties in barrier fabrics; however, there are some significant limitations. For example:

1) Water-based systems may require a surfactant or co-solvent. A surfactant can destabilize the fluorochemical, cause rewetting, and foaming. The choice of surfactant is very limited when compatibility with the fluorochemical and rewetting are considered. The surface tension required to wet polypropylene based materials is a surface tension below 32 dynes/centimeter. This is difficult to achieve and may result in uneven wetting of the fibers, especially the micro and nano denier types. Additionally, when very low porosity materials are treated, it may be difficult if not impossible to penetrate into the center of the barrier layers.

2) Water-based systems may require heat to dry and cure the fluorochemical. The exposure to high levels of heat may stiffen most fabrics, may result in tensile, burst, or tear strength loss, may drive off the antistat resulting in static control failure, and may yellow many fibers.

3) Water-based systems typically operate at only 1–5% solids. This may result in excessive use of energy to evaporate and drive off the water from the fabric. This may require more energy as the fiber diameter is reduced and surface area increases.

4) Water-based fluorochemical repellents used on naturally hydrophobic fibers tend to leave much of the fiber surfaces untreated. The untreated fibers may serve as a conduit for penetration and wicking of contaminants. Additionally, if an antistat is used in conjunction with a fluorochemical repellent, the antistat may migrate to the untreated fibers as it is repelled by the fluorochemical. The antistat is generally a higher surface energy material and may render sections of the barrier material non-repellent by raising the surface energy of the fibers and allowing them to wet by aqueous contaminants such as blood.

5) Fluorochemical dispersions generally have a cationic charge. Charged fluorochemical particles are preferentially attracted to negatively charged fiber surfaces and may deplete the finishing bath, and also may result in uneven deposition on the fiber. The uneven deposition may lead to untreated or poorly treated sections of the fiber and they may be sources of barrier failure, or conduits for antistat migration.

SUMMARY OF THE INVENTION

In view of the above discussion, a method of finishing a barrier fabric, according to embodiments of the present invention, includes applying a non-aqueous solution of low surface tension (e.g., surface tension less than about 40 dynes/cm) solvent and fluorochemical repellent to a barrier fabric, subjecting the barrier fabric to conditions sufficient to remove the solvent from the barrier fabric, and applying an aqueous-based antistat to a surface of the barrier fabric. The low surface tension solvent substantially covers all of the fiber's surface in the barrier fabric with the fluorochemical repellent. The treatment may be done in a way that completely treats the entire fabric, or can be oriented to one surface, such that the opposite surface has decreased repellency, or can be done in lanes or zones. As such, the antistat is prevented by the fluorochemical from migrating from the surface to which it is applied.

The non-aqueous solution can be applied to a barrier fabric in various ways including, but not limited to, saturating the barrier fabric with the non-aqueous solution, coating, spraying, or printing. Additionally, the solvent can be removed from the barrier fabric in various ways including, but not limited to, heating the barrier fabric, air drying the barrier fabric, subjecting the barrier fabric to vacuum, or in combination thereof. The antistat also can be applied to a barrier fabric in various ways including, but not limited to, applying the antistat as a foam, a print, or a coating. The antistat may include conductive particles.

Various types of barrier fabrics can be finished in accordance with embodiments of the present invention including, but not limited to, nonwoven fabrics, woven fabrics, and laminated fabrics with film barrier layers. Exemplary nonwoven fabrics may include, but are not limited to, spunbond fabrics, meltblown fabrics, flash spun fabrics, spunlaced fabrics, spunbond-meltblown-spunbond fabrics, and combinations thereof.

According to embodiments of the present invention, a method of finishing a barrier fabric includes applying a non-aqueous solution of a low-surface tension (e.g., surface tension of less than about 40 dynes/cm) solvent and fluorochemical repellent to a first surface of a barrier fabric, subjecting the barrier fabric to conditions sufficient to remove the solvent from the barrier fabric, and applying an aqueous-based antistat to the opposite, second surface of the barrier fabric. The low surface tension solvent substantially covers all fibers in the barrier fabric first surface with the fluorochemical repellent. As such, the antistat is prevented by the fluorochemical from migrating from the second surface to which it is applied to the first surface.

DETAILED DESCRIPTION OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patent applications, patents, and other references mentioned herein are incorporated herein by reference in their entireties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention.

According to embodiments of the present invention, a method of finishing a barrier fabric includes applying a non-aqueous solution to a barrier fabric, wherein the non-aqueous solution comprises a fluorochemical repellent and a low surface tension solvent, subjecting the barrier fabric to conditions sufficient to remove the solvent from the barrier fabric, and applying an aqueous-based antistat to a surface of the barrier fabric, wherein the antistat is prevented from migrating from the surface by the fluorochemical repellent. Applicants unexpectedly have discovered that if a fluorochemical repellent is dissolved in an organic solvent having low surface tension, for example a surface tension less than about 40 dynes/cm, when this solution is applied to the fibers of a barrier fabric, the fibers become uniquely treated in a uniform manner. Specifically, all of the fibers become wet with the solution and the fiber surfaces become completely covered with the low energy fluorochemical.

Because this treatment method is not a dispersion in water, there is no electrical charge to cause an uneven deposition, as is the case with conventional treatment methods. Additionally, since this treatment method is a fluorochemical dissolved in a solvent that already has a low surface tension, no surfactant is required for dispersion stability or for wetting the hydrophobic fiber surfaces. This eliminates rewetting caused by surfactants in conventional aqueous finishes.

Low surface tension solvents are well known to those having skill in the art of the present invention. Many, if not most, organic solvents have surface tension below about 40 dynes/cm. A non-exhaustive list of solvents (including their surface tension value) that may be used in accordance with embodiments of the present invention is set forth in the "CRC Handbook of Chemistry and Physics; $74^{th}$ edition; section 6; pp 144–147. However, any type of low surface tension solvent may be used in accordance with embodiments of the present invention. Embodiments of the present invention are not limited to any particular type of low surface tension solvent.

Embodiments of the present invention are particularly advantageous over conventional methods of finishing barrier fabrics. In conventional aqueous-based finishing methods an antistat and fluorochemical repellent are mixed in a ratio that results in the best compromise of repellency and antistatic properties. However, the mixture may separate upon drying, wherein the fluorochemical repels the antistat and results in very small but separate areas of treatment on the fiber surface. When applied on a fibrous barrier fabric, the results are such that no region will have a failure in repellency or static control; however, if any of the hydrophobic fibers are not completely treated by the fluorochemical, the antistat may migrate to areas and degrade the repellency. With the solvent based method, this cannot happen due to the uniformity of the wetting by the repellent treatment and the separate application of the antistat.

The non-aqueous solution can be applied to a barrier fabric in various ways including, but not limited to, saturating the barrier fabric with the non-aqueous solution, coating the first surface of the barrier fabric using a slot coater, knife coater, kiss coater, gravure coater, flexo coater, or printing the non aqueous solution using screen, rotogravure, or flexographic printers, or passing through a horizontal nip either directly through or wrapped on one roll, or by spraying. The non-aqueous solution may be applied as a, paste, or liquid, and may be warmed to speed the evaporation. Additionally, the solvent can be removed from the barrier fabric in various ways including, but not limited to, heating the barrier fabric, air drying the barrier fabric, subjecting the barrier fabric to vacuum, or in combination thereof.

The antistat also can be applied to a barrier fabric in various ways including, but not limited to, coating the first surface of the barrier fabric using a slot coater, knife coater, kiss coater, gravure coater, flexo coater, or printing the non aqueous solution using screen, rotogravure, or flexographic printers, or by spraying. The antistatic formulation may be formulated as a foam, paste, or liquid, may contain salts, organic antistats, or conductive particles (e.g., carbon, silver-coated copper, metallized glass beads, iron powder, etc.), and may be warmed to speed the evaporation.

Various types of barrier fabrics can be finished in accordance with embodiments of the present invention including, but not limited to, nonwoven fabrics, woven fabrics, and laminated fabrics with film barrier layers. Exemplary nonwoven fabrics may include, but are not limited to, spunbond fabrics, meltblown fabrics, flash spun fabrics, spunlaced fabrics, spunbond-meltblown-spunbond fabrics, and combinations thereof.

Spunbonded fabrics are described in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, and U.S. Pat. No. 5,643,653 to Griesbach, III et al., each of which is incorporated herein by reference in its entirety. Spunbond fabrics conventionally contain fibers greater than about ten microns (10μ) in diameter and conventionally are made from thermoplastic polymers such as polyolefins, polyamides, or polyesters.

Meltblown fibers and meltblown fabrics conventionally are produced by extruding thermoplastic polymer through a fine orifice and subsequently exposing the polymer stream to a jet of high velocity air. Meltblown fibers conventionally are less than about ten microns (10μ) in diameter. Meltblown fibers and fabrics are described in U.S. Pat. No. 3,849,241 to Buntin et al., U.S. Pat. No. 4,307,143 to Meitner, and U.S. Pat. No. 4,663,220 to Wisneski et al., each of which is incorporated herein by reference in its entirety.

Another fabric conventionally used in barrier applications, and which may be finished in accordance with embodiments of the present invention, is Tyvek® brand plexifilimentary flash spun polyethylene from DuPont. Fabrics of this type are disclosed in U.S. Pat. No. 3,081,519 to Blades et al., which is incorporated herein by reference in its entirety.

Another fabric conventionally used in barrier applications, and which may be finished in accordance with embodiments of the present invention, is Evolon® brand spunbond/spunlaced fabric. This fabric is composed of splittable filaments that, when split in the spunlace process, result in fine fibers with good barrier properties. For example, U.S. Pat. Nos. 5,899,785 and 5,970,583 to Groten et al., both assigned to Freudenberg and incorporated herein by reference in their entireties, describe a nonwoven lap of very fine continuous filament and the process for making such nonwoven lap using traditional nonwoven manufacturing techniques. The raw material for this process is a spun-bonded composite, or multi-component fiber that is splittable along its length by mechanical or chemical action. As an example, after a nonwoven lap is formed, it may be subjected to high-pressure water jets which cause the composite fibers to partially separate along their length and become entangled with one another thereby imparting strength and microfiber-like softness to the final product. One such product manufactured and made available by Freudenberg according to these processes is known as Evolon® Brand fabric.

Another fabric conventionally used in barrier applications, and which may be finished in accordance with embodiments of the present invention, is Suprel® brand fabric from DuPont. Suprel® brand fabric is an SMS type fabric that often contains polyethylene in the meltblown component or in the sheath of the fibers of the spunbond component. Fabrics of this type are described in U.S. Pat. No. 5,885,909 to Rudisill et al., which is incorporated herein by reference in its entirety.

Woven fabrics used in surgical barrier products may be finished in accordance with embodiments of the present invention. Woven barrier fabrics conventionally are constructed from fine denier synthetic yarn and woven tightly to produce a barrier structure. Fabrics of this type are described in U.S. Pat. Nos. 4,822,667 and 4,919,998 to Goad et al., and each of which is incorporated herein by reference in its entirety.

Laminated fabrics with film barrier layers may be finished in accordance with embodiments of the present invention. Fabrics with at least one layer of fabric and a second layer of barrier material bonded to the fabric layer can be treated. Fabrics with film layers, microporous film laminated such as described in U.S. Pat. No. 5,560,974 to Langley (which is incorporated herein by reference in its entirety), or fabrics with a microporous PTFE membrane as described in U.S. Pat. No. 4,187,390 to Gore (which is incorporated herein by reference in its entirety), or microporous polypropylene laminated structures as described in U.S. Pat. No. 5,843,057 to McCormack, or U.S. Pat. No. 5,503,907 to Gessner et al. (each of which is incorporated herein by reference in its entirety), would be appropriately treated.

In addition, nonwoven fabrics comprised of woodpulp, rayon, lyocell, or other cellulosic materials may be finished in accordance with embodiments of the present invention.

According to embodiments of the present invention, a substrate may be treated fully with the solvent based system and then the antistat topically applied to one surface via coating, spraying or printing, or alternately, the solvent based fluorochemical can be topically applied to one side and the antistat applied to the other. This may be especially effective in the solvent fluorochemical system since the fluorochemical treatment is so uniform, it prohibits the migration of the antistat into the barrier region. The antistat portion of the treatment is done with water. The water-based system is held on the applied surface by the repellent body of the fabric. If the antistat is mixed with the fluorochemical then the surface energy is lowered and the barrier is compromised.

EXAMPLE 1

Application of Fluorochemical and Antistat

One side (Side "A") of a 1.50-osy SMS (spunbond-meltblown-spunbond) nonwoven was treated with a solvent-soluble fluorochemical dispersion at a wet pick-up of 35%. The fluorochemical was a dispersion of Mitsubishi Corporation's Repearl Grade F-622 dispersed in n-propyl bromide (2% solids and 1% fluorine). The fabric was either air-cured for 5 minutes at room temperature, or cured on a production vertical pin tenter frame with direct gas fired heating (170° F. fabric temperature) for <30 seconds.

The other side (Side "B") of the 1.50-osy SMS was treated with an aqueous/solvent-based antistat that was foamed in a Hobart mixer to a blow ratio of 18:1 and applied via a knife coater at a gap of 0.004" (wet pickup of 30%). The antistat was Cytec's Cyastat SN (quaternary ammonium nitrate) dispersed in de-ionized water (0.15% as received). The treated fabric was dried at 70° C. for 30 seconds in a laboratory vertical pin tenter frame.

| Property | Unit | Direction | Test Data (n = 6) | |
| --- | --- | --- | --- | --- |
| | | | 3657-50000[A] | 3657-50001[B] |
| Basis Weight | osy | | 1.47 | 1.47 |
| Water Impact | gm | | 0.08 | 0.29 |
| Grab Tensile | lb | MD | 26.6 | 26.0 |
| | | CD | 15.9 | 15.6 |
| Grab Elongation | % | MD | 57.9 | 55.7 |
| | | CD | 101.5 | 91.5 |
| Trapezoid Tear | lb | MD | 5.9 | 5.2 |
| | | CD | 10.3 | 10.1 |
| Porosity | cfm | | 46.9 | 47.3 |
| HOM | g | MD | 65.6 | 59.1 |
| | | CD | 30.7 | 36.3 |
| Alcohol Rating (Side "A") | rating | | 9.0 | 9.5 |
| Hydrohead | cm | | 77.4 | 75.0 |
| Martindale | mg | | 8.8 | 7.7 |
| Circular Bend | kg | MD | 211 | 220 |
| Static Decay @ 50% RH | sec | MD | No charge | 0.01 |

[A]Side "A" - First-pass fluorochemical treatment.
[B]Side "B" - Second-pass antistat treatment.

EXAMPLE 2

Application of Fluorochemical and Gravure Application of Antistat

One side (Side "A") of a 1.50-osy SMS (spunbond-meltblown-spunbond) nonwoven was treated with a solvent-soluble fluorochemical dispersion at a wet pick-up of 35%. The fluorochemical was a dispersion of Mitsubishi Corporation's Repearl Grade F-622 dispersed in n-propyl bromide (2% solids and 1% fluorine). The fabric was either air-cured for 5 minutes at room temperature, or cured on a production vertical pin tenter frame with direct gas fired heating (170° F. fabric temperature) for less than about 30 seconds.

The other side (Side "B") of the 1.50-osy SMS was treated with an aqueous/solvent-based antistat that was applied via gravure coating using a 220 quad cylinder controlled to a wet pickup from 15 to 50%. The antistat was Stepan's Zelec TY (phosphate ester) dispersed in 0.3 to 0.6% Alfol 06 (1-Hexanol) and de-ionized water (0.5 to 0.7% as received). The treated fabric was dried at 70° C. for 30 seconds in a laboratory pin tenter frame.

| Zelec TY, % | Alfol 06, % | WPU | Alcohol Rating (Side A) | Test Data (n = 6)[A] | | | | | |
| --- | --- | --- | --- | --- | --- | --- | --- | --- | --- |
| | | | | HH, cm | | SD20 MD | | SD20 CD | |
| | | | | 8/20 | 8/27 | 8/20 | 8/27 | 8/20 | 8/27 |
| 0.7 | 0.3 | 35.3 | 9.0 | 84.7 | 83.3 | 0.13 | 0.14 | 0.09 | 0.44 |
| 0.7 | 0.6 | 34.0 | 9.0 | 85.5 | 92.6 | 0.05 | 0.10 | 0.06 | 0.25 |

EXAMPLE 3

Gravure Application of Fluorochemical and Antistat

One side (Side "A") of a 1.50-osy SMS (spunbond-meltblown-spunbond) nonwoven was treated with a solvent-soluble fluorochemical dispersion via a gravure coating using a 35 quad cylinder controlled to a wet pickup from 60 to 100%. The fluorochemical was a dispersion of Mitsubishi Corporation's Repearl Grade F-622 dispersed in n-propyl bromide (0.16 to 0.25% solids). The fabric was either air-cured for 5 minutes at room temperature, or cured on a production vertical pin tenter frame with direct gas fired heating (170° F. fabric temperature) for <30 seconds.

The other side (Side "B") of the 1.50-osy SMS was treated with an aqueous/solvent-based antistat that was applied via gravure coating using a 220 quad cylinder controlled to a wet pickup from 15 to 50%. The antistat was Stepan's Zelec TY (phosphate ester) dispersed in 0.3 to 0.6% Alfol 06 (1-Hexanol) and de-ionized water (0.21% as received). The treated fabric was dried at 70° C. for 30 seconds in a laboratory vertical pin tenter frame.

| F-622, % solids | Zelec TY, % as received | Alcohol Rating | Hydrohead, cm | Static Decay, sec (50% RH) |
|---|---|---|---|---|
| 0.16 | 0.21 | 7.0 | n.t. | 0.02 |
| 0.03 | 0.21 | 5.0 | n.t. | 0.02 |
| 0.06 | 0.21 | 6.0 | 80.6 | 0.02 |
| 0.13 | 0.21 | 8.0 | 83.4 | 0.02 |
| 0.25 | 0.21 | 8.0 | 88.2 | 0.02 | n.t. = not tested.

EXAMPLE 4

Screen Printing Antistatic Chemicals to SMS

A 1.5osy SMS nonwoven was solvent treated on the front side with a fluorochemical to give it an alcohol repellency of 9. An antistatic treatment was then applied in a grid pattern using the method of screen printing on the back side of the fabric to give a static decay value of less then 30 seconds at 20% RH and 70° F. The treatment was made in aqueous based solutions at levels of 1.5–4% as received antistat and thickened. It was applied through the screen with minimal pressure so that it remained on the surface of the fabric, avoiding penetration into the melt blown layer of the fabric. At 4% Zelec TY (as received) OWB, the static decay values at 20% RH and 70° F. were +2.33 s and −2.13 s.

The foregoing is illustrative of the present invention and is not to be construed as limiting thereof. Although a few exemplary embodiments of this invention have been described and several examples provided, those skilled in the art will readily appreciate that many modifications are possible in the exemplary embodiments without materially departing from the novel teachings and advantages of this invention.

That which is claimed is:

1. A method of finishing a barrier fabric, comprising:
applying a non-aqueous solution to a barrier fabric, wherein the non-aqueous solution comprises a fluorochemical repellent and a low surface tension organic solvent, wherein the organic solvent is a non-aqueous organic solvent having a surface tension at 25° C. of between 11 dynes/cm and 40 dynes/cm;
removing the organic solvent from the barrier fabric by heating the barrier fabric and/or air drying the barrier fabric and/or subjecting the barrier fabric to vacuum; and
applying an aqueous-based antistat to a surface of the barrier fabric, wherein the antistat is prevented from migrating from the surface by the fluorochemical repellent.

2. The method of claim 1, wherein applying a non-aqueous solution to a barrier fabric comprises spraying the non-aqueous solution onto the barrier fabric.

3. The method of claim 1, wherein applying a non-aqueous solution to a barrier fabric comprises saturating the barrier fabric with the non-aqueous solution.

4. The method of claim 1, wherein applying a non-aqueous solution to a barrier fabric comprises printing the non-aqueous solution onto the barrier fabric.

5. The method of claim 1, wherein applying a non-aqueous solution to a barrier fabric comprises coating the barrier fabric with the non-aqueous solution.

6. The method of claim 1, wherein applying an aqueous-based antistat to a surface of the substrate comprises applying the antistat as a foam.

7. The method of claim 1, wherein applying an aqueous-based antistat to a surface of the substrate comprises printing the antistat onto the substrate surface.

8. The method of claim 1, wherein applying an aqueous-based antistat to a surface of the substrate comprises spraying the antistat onto the substrate surface.

9. The method of claim 1, wherein applying an aqueous-based antistat to a surface of the substrate comprises coating the substrate surface with the antistat.

10. The method of claim 1, wherein the antistat comprises conductive particles.

11. The method of claim 1, wherein the barrier fabric comprises nonwoven fabric.

12. The method of claim 11, wherein the nonwoven fabric is selected from the group consisting of spunbond fabrics, meltblown fabrics, flash spun fabrics, spunlaced fabrics, spunbond-meltblown-spunbond fabrics, and combinations thereof.

13. The method of claim 1, wherein the barrier fabric comprises woven fabric.

14. The method of claim 1, wherein the barrier fabric comprises laminated fabrics having film barrier layers.

15. A method of finishing a barrier fabric, wherein the barrier fabric includes opposite first and second surfaces, comprising:
applying a non-aqueous solution to the barrier fabric first surface, wherein the non-aqueous solution comprises a fluorochemical repellent and a low surface tension organic solvent, wherein the organic solvent is a non-aqueous organic solvent having a surface tension at 25° C. of between 11 dynes/cm and 40 dynes/cm;
removing the organic solvent from the barrier fabric by heating the barrier fabric and/or air drying the barrier fabric and/or subjecting the barrier fabric to vacuum; and
applying an aqueous-based antistat to the barrier fabric second surface, wherein the antistat is prevented from migrating from the second surface by the fluorochemical repellent.

16. The method of claim 15, wherein applying an aqueous-based antistat to one surface of the substrate comprises applying the antistat as a foam.

17. The method of claim 15, wherein applying an aqueous-based antistat to the barrier fabric second surface comprises printing the antistat onto the barrier fabric second surface.

18. The method of claim 15, wherein applying an aqueous-based antistat to the barrier fabric second surface comprises spraying the antistat onto the barrier fabric second surface.

19. The method of claim 15, wherein applying an aqueous-based antistat to the barrier fabric second surface comprises coating the barrier fabric second surface with the antistat.

20. The method of claim 19, wherein the antistat comprises conductive particles.

21. The method of claim 15, wherein the barrier fabric comprises nonwoven fabric.

22. The method of claim 21, wherein the nonwoven fabric is selected from the group consisting of spunbond fabrics, meltblown fabrics, flash spun fabrics, spunlaced fabrics, spunbond-meltblown-spunbond fabrics, and combinations thereof.

23. The method of claim 15, wherein the barrier fabric comprises woven fabric.

24. The method of claim 15, wherein the barrier fabric comprises laminated fabrics having film barrier layers.

25. A method of finishing a nonwoven barrier fabric, wherein the barrier fabric includes opposite first and second surfaces, comprising:

applying a non-aqueous solution to the barrier fabric first surface, wherein the non-aqueous solution comprises a fluorochemical repellent and a low surface tension organic solvent, wherein the organic solvent is a non-aqueous organic solvent having a surface tension at 25° C. of between 11 dynes/cm and 40 dynes/cm, and wherein the low surface organic tension solvent substantially covers all fibers at the barrier fabric first surface with the fluorochemical repellent;

removing the organic solvent from the barrier fabric by heating the barrier fabric and/or air drying the barrier fabric and/or subjecting the barrier fabric to vacuum; and applying an aqueous-based antistat to the barrier fabric second surface, wherein the antistat is prevented from migrating from the second surface by the fluorochemical repellent.

26. The method of claim 25, wherein applying an aqueous-based antistat to one surface of the substrate comprises applying the antistat as a foam.

27. The method of claim 25, wherein the nonwoven fabric is selected from the group consisting of spunbond fabrics, meltblown fabrics, flash spun fabrics, spunlaced fabrics, spunbond-meltblown-spunbond fabrics, and combinations thereof.

* * * * *